United States Patent
Horiuchi et al.

(10) Patent No.: US 9,464,307 B2
(45) Date of Patent: Oct. 11, 2016

(54) METHOD FOR GENE AMPLIFICATION

(71) Applicant: Genodive Pharma Inc., Kanagawa (JP)

(72) Inventors: Takashi Horiuchi, Aichi (JP); Takaaki Watanabe, Los Angeles, CA (US)

(73) Assignee: GENODIVE PHARMA INC., Kanagawa (JP)

( * ) Notice: Subject to any disclaimer, the term of this patent is extended or adjusted under 35 U.S.C. 154(b) by 492 days.

(21) Appl. No.: 13/890,533

(22) Filed: May 9, 2013

(65) Prior Publication Data

US 2013/0266988 A1 Oct. 10, 2013

Related U.S. Application Data

(63) Continuation of application No. 12/085,476, filed as application No. PCT/JP2006/314168 on Jul. 18, 2006, now abandoned.

(30) Foreign Application Priority Data

Nov. 24, 2005 (JP) ................. 2005-338119

(51) Int. Cl.
C12P 19/34 (2006.01)
C12Q 1/68 (2006.01)

(52) U.S. Cl.
CPC ............. *C12P 19/34* (2013.01); *C12Q 1/6844* (2013.01); *C12Q 1/6867* (2013.01)

(58) Field of Classification Search
None
See application file for complete search history.

(56) References Cited

U.S. PATENT DOCUMENTS

| | | |
|---|---|---|
| 6,255,082 B1 | 7/2001 | Lizardi |
| 2007/0249016 A1 | 10/2007 | Horiuchi et al. |
| 2009/0148895 A1 | 6/2009 | Horiuchi et al. |

FOREIGN PATENT DOCUMENTS

| | | |
|---|---|---|
| EP | 1 707 626 A1 | 10/2006 |
| WO | WO94/14968 | 7/1994 |
| WO | WO02/40685 | 5/2002 |
| WO | WO2005/001087 | 1/2005 |
| WO | WO2005/061703 | 7/2005 |
| WO | WO2007/060764 | 5/2007 |

OTHER PUBLICATIONS

Langer et al. (Nucleic Acids Research, 2002, 30(14):3067-3077).*
Campo et al. (2002, Appl. Envr. Microbiol, 68(5):2359-2367).*
Branda et al. (Developmental Cell, 2004, vol. 7, p. 6-28, IDS reference).*
Watanabe et al (EMBO journal, 2005, vol. 24, p. 190-198).*

(Continued)

*Primary Examiner* — Stephanie K Mummert
(74) *Attorney, Agent, or Firm* — Carol L. Francis; Bozicevic, Field & Francis LLP

(57) ABSTRACT

The present invention provides a double-stranded DNA constructed specifically for high speed gene amplification, a method for gene amplification and a method for synthesizing protein. The gene amplification system of the present invention used a site-specific recombinase such as Cre-lox system and target sequence thereof to efficiently induce a type of replication referred to as a double rolling-circle replication (DRCR). Amplification unit, whose structure is shown in FIG. 2 (*a*), is constructed in animal and other cells. DRCR is induced by two recombination events triggered by a site-specific recombinase (Cre) when each replication folk progresses between each pair of target sequences (lox sequences).

15 Claims, 7 Drawing Sheets

(56) References Cited

OTHER PUBLICATIONS

Watanabe et al., "Gene amplification system based on double rolling-circle replication as a model for oncogene-type amplification," Nucleic Acids Research. vol. 39, No. 16 p. e106 (2011).
Branda, C.S., and Dymecki, S.M., "Talking about a Revolution: The Impact of Site-Specific Recombinases on Genetic Analyses in Mice," Developmental Cell. vol. 6 pp. 7-28 (2004).
Butler et al., "Formation of Large Palindromic DNA by Homologous Recombination of Short Inverted Repeat Sequences in *Saccharomyces cerevisiae*," Genetics. vol. 161 pp. 1065-1075 (2002).
Campo et al., "Cre-*loxP* Recombination System for Large Genome Rearrangements in *Lactococcus lactis*," Applied and Environmental Microbiology. vol. 68, No. 5 pp. 2359-2367 (2002).
Dong, Z., and Fasullo, M., "Multiple recombination pathways for sister chromatid exchange in *Saccharomyces cerevisiae*: role of *RAD1* and the *RAD52* epistasis group genes," Nucleic Acids Research. vol. 31, No. 10 pp. 2576-2585 (2003).
Extended European Search Report corresponding to European Patent Application No. 06768267.4-1222 dated Jun. 4, 2010.
Genbank Accession No. AF298782. Guldener et al., "A second set of loxP marker cassettes for Cre-mediated multiple gene knockouts in budding yeast," Nucleic Acids Research. vol. 30, No. 6 p. E23 (2002).
Genbank Accession No. NC-001138. Goffeau et al., "Life with 6000 genes," Science. vol. 274, No. 5287 p. 546 (1996).
International Preliminary Report on Patentability (Chapter I of the Patent Cooperation Treaty) corresponding to International Patent Application No. PCT/JP2004/016833 dated Jul. 24, 2006.
International Preliminary Report on Patentability (Chapter I of the Patent Cooperation Treaty) corresponding to International Patent Application No. PCT/JP2006/314168 dated May 27, 2008.
International Search Report corresponding to International Patent Application No. PCT/JP2004/016833 dated May 17, 2005.
International Search Report corresponding to International Application No. PCT/JP2006/314168 dated Sep. 12, 2006.
Interview Summary corresponding to U.S. Appl. No. 12/085,476 dated Oct. 25, 2011.
Interview Summary corresponding to U.S. Appl. No. 12/085,476 dated Mar. 12, 2013.
Kim et al., "In vivo excision and amplification of large human genomic segments using the Cre/loxP-and large T antigen/SV40 ori-mediated machinery," Journal of Biotechnology. vol. 110, No. 3 pp. 227-233 (2004).
Kraus et al., "Break-induced replication: A review and an example in budding yeast," PNAS. vol. 98, No. 15 pp. 8255-8262 (2001).
Langer et al., "A genetic screen identifies novel non-compatible *loxP* sites," Nucleic Acids Research. vol. 30, No. 14 pp. 3067-3077 (2002).
Lankenau et al., "Knockout Targeting of the *Drosophila Nap1* Gene and Examination of DNA Repair Tracts in the Recombination Products," Genetics. vol. 163, No. 2 pp. 611-623 (2003).
Malkova et al., "RAD51-independent break-induced replication to repair a broken chromosome depends on a distant enhancer site," Genes & Development. vol. 15, No. 9 pp. 1055-1060 (2001).
Merker et al., "Patterns of Heteroduplex Formation Associated With the Initiation of Meiotic Recombination in the Yeast *Saccharomyces cerevisiae*," Genetics. vol. 165, No. 1 pp. 47-63 (2003).
Narayanan et al., "The Pattern of Gene Amplification is Determined by the Chromosomal Location of Hairpin-Capped Breaks," Cell. vol. 125, No. 7 pp. 1283-1296 (2006).
Official Action corresponding to U.S. Appl. No. 10/580,424 dated Apr. 21, 2008.
Official Action corresponding to U.S. Appl. No. 12/085,476 dated Sep. 15, 2010.
Official Action corresponding to U.S. Appl. No. 12/085,476 dated Jan. 5, 2011.
Official Action corresponding to U.S. Appl. No. 12/085,476 dated Jul. 11, 2011.
Official Action corresponding to U.S. Appl. No. 12/085,476 dated Mar. 1, 2012.
Official Action corresponding to U.S. Appl. No. 12/085,476 dated Nov. 9, 2012.
Rattray et al., "A mechanism of palidromic gene amplification in *Saccharomyces cerevisiae*," Genes and Development. vol. 19 pp. 1390-1399 (2005).
Rattray et al., "Fidelity of Mitotic Double-Strand-Break Repair in *Saccharomyces cerevisiae*: A Role for *SAE2/COM1*," Genetics. vol. 158, No. 1 pp. 109-122 (2001).
Richardson et al., "Double-strand break repair by interchromosomal recombination: suppression of chromosomal translocations," Genes & Development. vol. 12 pp. 3831-3842 (1998).
Sektas, M., and Specht, M., "Limited use of the Cre/1oxP Recombination system in efficient production of 1oxP-containing minicircles in vivo," Plasmid. vol. 53, No. 2 pp. 148-163 (2005).
Signon et al., "Genetic Requirements for *RAD51*- and *RAD54*- Independent Break-Induced Replication Repair of a Chromosomal Double-Strand Break," Molecular and Cellular Biology. vol. 21, No. 6 pp. 2048-2056 (2001).
Stark, G.R., and Wahl, G.M., "Gene Amplification," Ann. Rev. Biochem. vol. 53 pp. 447-491 (1984).
Volkert, F.C., and Broach, J.R., "Site-specific recombination promotes plasmid amplification in yeast," Cell. vol. 46, No. 4 pp. 541-550 (1986).
Watanabe, T., and Horiuchi, T., "A novel gene amplification system in yeast based on double rolling-circle replication," The Embo Journal. vol. 24, No. 1 pp. 190-198 (2005).
Watanabe, T., and Horiuchi, T., "Development of a novel gene amplification system utilizing break-induced replication," The Molecular Biology Society of Japan Program. vol. 26 p. 418 (2003).

* cited by examiner

| | |
|---|---|
| ○ | Replication Origin |
| ➡ | leu2d |
| ▷ | loxP |
| ▶ | loxm2 |
| □ | TRP1 |
| ▨ | LYS5 |

METHOD FOR GENE AMPLIFICATION

CROSS-REFERENCE TO RELATED APPLICATIONS

This application is a continuation of U.S. patent application Ser. No. 12/085,476, filed on May 23, 2008, which is a national stage application of International Application No. PCT/JP2006/314168, filed on Jul. 18, 2006, and which claims benefit of Japanese Patent Application No. 2005-338119 filed Nov. 24, 2005, the disclosures of each of which are incorporated herein in their entireties.

CROSS-REFERENCE TO RELATED DOCUMENTS

This application comprises a sequence listing filed in electronic form as an ASCII .txt file entitled 1680-26-2ST25.txt, created May 9, 2013, 2200 bytes (22 kilobytes). The content of the sequence listing is incorporated herein in its entirety.

FIELD OF THE INVENTION

The present invention relates to a method for amplifying gene at high speed and a method for producing proteins by using the amplified gene.

PRIOR ART

Gene amplification with cultured animal cells (Reference 1 and the like) accompanies several complications such as (1) time consuming (a half to one year), (2) presence of clones without amplification, and (3) empirical procedures with unexplained mechanism. On the other hand, there is no system of gene amplification with yeast. Although plasmids are generally used for the purpose, increase in copy number beyond a certain threshold is difficult.

The system of the present invention is based on the replication referred to as DRCR (Double Rolling-Circle Replication) induced by biological potency called as BIR (Break-Induced-Replication) (Reference 2-4). It is conceivable that a chromosome breakage is rescued itself by the following steps; i.e. the broken chromosome finds homologous sequence, invades into it, forms a replication fork, and consequently starts DNA replication. All living organisms might involve such ability.

Moreover, it is reported that natural circular DNA accompanies DRCR by recombination (Reference 5).

Reference 1: Japanese Patent Gazette 8-504585 (WO94/14968) Reference 2: WO2005/061703
Reference 3: PNAS, vol. 98, no. 15, 8255-8262 (Jul. 17, 2001)
Reference 4: Genes Dev 12, 3831-3842 (1998)
Reference 5: Cell. 1986 Aug. 15; 46 (4): 541-550

Problems to be Solved by the Invention

The present invention provides a double-stranded DNA constructed specially for high speed gene amplification, a method for gene amplification thereby and protein production thereby. The present invention is characteristic in full artificially designed system of gene amplification, the potential of higher amplification efficiency by synchronous culture, short period for amplification (probably one generation) and well elucidated mechanism of amplification.

Means to Solve the Problems

The amplification system of the present invention utilizes a type of DNA replication referred to as double rolling-circle replication (DRCR). The type of replication is able to amplify DNA explosively in a single cell cycle. It is assumed that the amplified products are maintained intracellularly after termination of DRCR by recombination and the like. The present inventors utilized a site-specific recombinase such as Cre-lox system and its target sequence in order to induce DRCR efficiently. More specifically, the present inventors constructed a replication unit (ex. FIG. 3) in yeast and were able to succeed in inducing DRCR by utilizing a recombination generated by a site-specific Cre recombinase (hereinafter, referred to as "Cre") during progress of a replication fork between a pair of lox sequences and to accomplish the present invention.

Namely, the present invention is a double-stranded DNA represented by a-b-c-d or a-c-b-d, wherein one of a and b is a double-stranded DNA fragment comprising a first target sequence of a site-specific recombinase, and the other is a double-stranded DNA fragment comprising an inverted sequence of said first target sequence; and one of c and d is a double-stranded DNA fragment comprising a second target sequence of the site-specific recombinase and the other is a double-stranded DNA fragment comprising an inverted sequence of said second target sequence; a replication origin and at least one target gene to be amplified are inserted anywhere between a and d; and arbitrary DNA sequences may be inserted among above fragments.

Additionally, the present invention is a recombinant vector comprising the double-stranded DNA, and is also a transformant, which is introduced with the double-stranded DNA.

Moreover, the present invention is a set of double-stranded DNA comprising a double-stranded DNA fragment represented by e-a-A-b-f and a double-stranded DNA fragment represented by g-c-B-d-h, wherein one of a and b is a double-stranded DNA fragment comprising a first target sequence of a site-specific recombinase, and the other is a double-stranded DNA fragment comprising an inverted sequence of said first target sequence; and one of c and d is a double-stranded DNA fragment comprising a second target sequence of the site-specific recombinase and the other is a double-stranded DNA fragment comprising an inverted sequence of said second target sequence; each of letters from e to h is a double-stranded DNA fragment of at least 50 bp in size, which are arranged on a chromosome or an extrachromosomal element that is a host for integration of the set of double-stranded DNA in order of e, f, a replication origin of the chromosome element or the extrachromosomal element, g and h; at least one of A and B represents the target gene to be amplified; and said replication origin or a part of it may be included in f or g; and an arbitrary DNA sequence may be inserted among these.

The present invention is also a set of recombinant vectors, wherein each vector contains each of two kinds of the double-stranded DNA, and is also a transformant or transfectant, which is introduced with two kinds of the double-stranded DNA, wherein said replication origin locates on a host chromosome or an extrachromosome.

The present invention is also a method for amplifying the target gene, comprising the steps of preparing the transformant or the transfectant and affecting said transformants with the site-specific recombinase; and is a method for manufacturing a protein encoded by the target gene, comprising a step of culturing transformed or transfected cells obtained by the above method.

Effects of the Invention

The amplification system of the present invention has an excellent property in establishing efficient system for producing proteins. DRCR is capable of amplifying a target gene rapidly during a single cell cycle. Since the amplification mechanism is well elucidated, reliable amplification of a target gene is prospective. Although the present example was constructed in yeast not animal cells, it is possible to produce highly amplified products at 10 to 100 times higher frequency than a conventional system of animal cultured cells. Furthermore, the present system can be applied to primary cultured cells, in which gene amplification by drug selection has not been observed. Therefore, it is possible to apply gene amplification to targeting cells of gene therapy, and to enhance and sustain the expression of introduced gene.

DETAILED DESCRIPTION OF THE INVENTION

Figure 1:
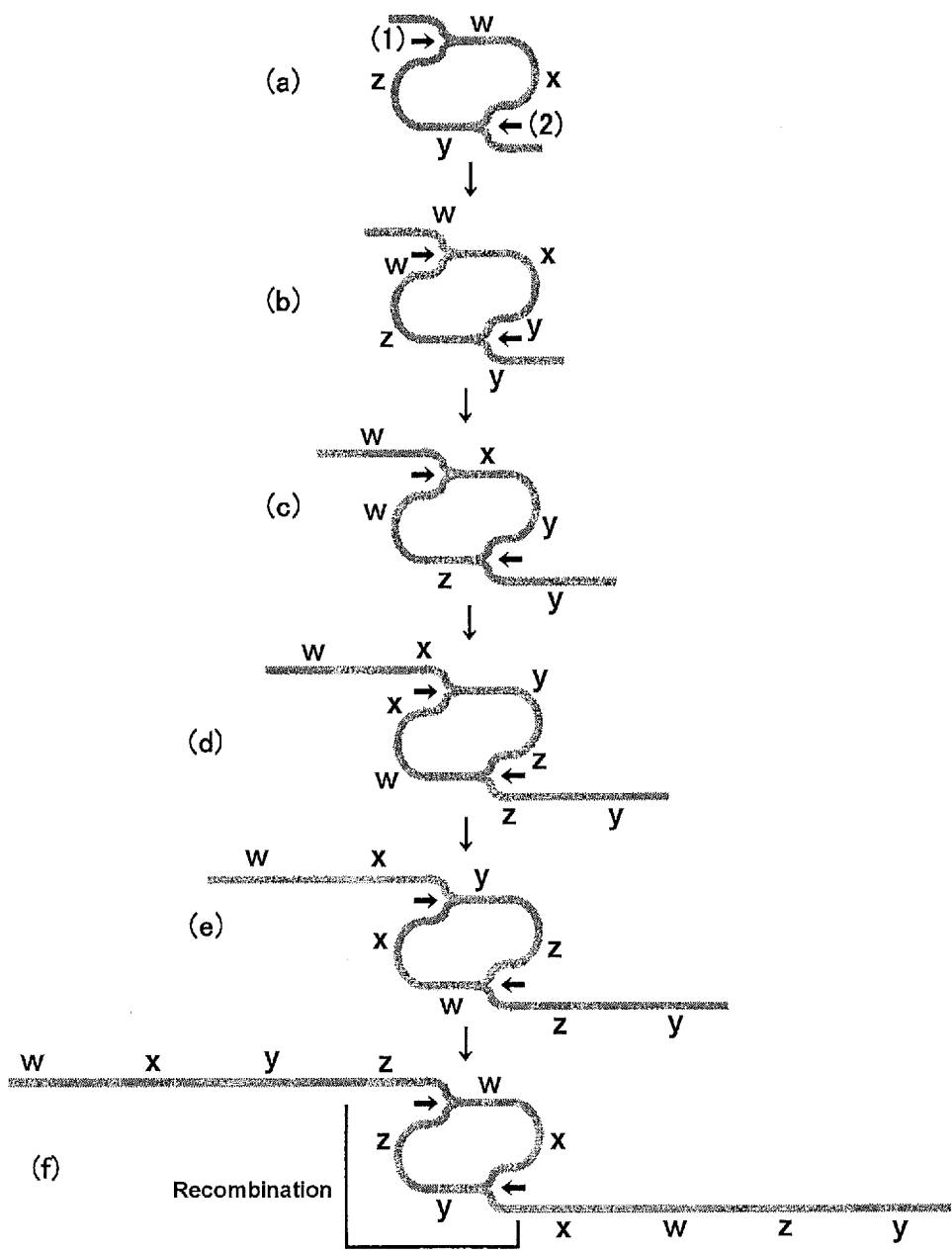
FIG. 1 shows a DRCR reaction. Black arrowheads show replication folks.

The gene amplification method of the present invention utilizes a double rolling-circle replication (DRCR), which enables a rapid amplification, and is presumed to be functional both in budding yeasts and in animal cells. The gene amplification system is a type of DNA replication, wherein two replication folks replicate continuously a circular DNA, as shown in FIG. 1. In the beginning, folk (1) replicates w and folk (2) replicates y ((a), (b), (c)), then folk (1) and folk (2) replicates x and folk (2) replicates z ((c), (d), (e)). In this way, the replication continues endlessly, since a template for one folk is synthesized by the other folk successively.

After the amplification has proceeded, the central circular form seems to be removed by recombination and the like, and the reaction seems to be terminated (f).

The gene amplification system of the present invention utilizes a site-specific recombination, which is known to be functional even in animal cells, in order to induce DRCR. This reaction is a reversal of DNA replication by recombination during progression of the replication folk between a set of target sequences. A pair of the reactions is used for the amplification system.

Figure 2:
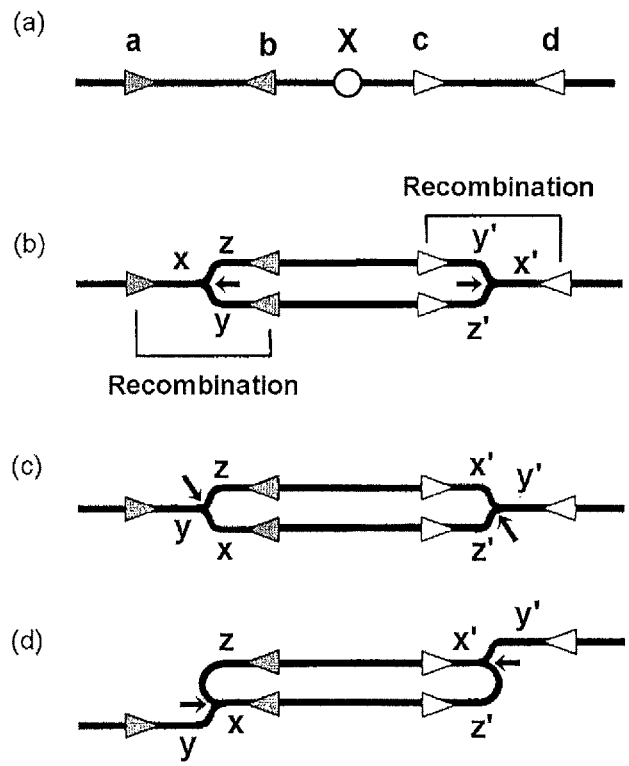
FIG. 2 shows the initiation of the amplification reaction by using a site-specific recombinase and its target sequences. The triangular arrowheads (letters from a to d) represent the target sequences (e.g. loxP sequence) of a site-specific recombinase and the direction thereof. X represents replication origin (and so forth). Letters from x to z and x' to z' represent genes to be amplified. Black arrows represent replication folks.

Namely, in the amplification system of the present invention, firstly, DNA replication starts in the amplification unit constructed as in FIG. 2 (*a*). Secondly, the two replication folks represented by black arrows go just between two sets of target sequences (lox sequences) of a site-specific recombinase (e.g. Cre). Lastly, the target sequences (e.g. loxP sequences) on parent DNA strand x and x' recombine with the target sequences (e.g. loxP sequences) on de novo DNA strand y and y', respectively. After the recombination events, one of the folks synthesizes y and z strands from x strand and the other folk synthesizes y' and z' strands from x' strand (FIG. 2 (*c*)). In this way, the progress of each replication folk is reversed and the replicated DNA strands are replicated again (FIG. 2 (*d*)). DRCR is carried out by these two reactions.

The double-stranded DNA used in the present invention is represented by a-b-c-d or a-c-b-d, or preferably by a-b-c-d.

One of a and b represents a double-stranded DNA fragment comprising a first target sequence of a site-specific recombinase, and the other represents a double-stranded DNA fragment comprising inverted sequence of the first target sequence of the site-specific recombinase. One of c and d represents a double-stranded DNA fragment comprising a second target sequence of a site-specific recombinase, and the other represents a double-stranded DNA fragment comprising inverted sequence of the second target sequence of the site-specific recombinase. The first target sequence could be the same as the second target sequence, but is preferably different from the later. Additionally, arbitrary DNA sequence may be inserted between these sequences.

The above b and c may be combined and the DNA may be represented by a-b-d, wherein d and a represent the same target sequence with the same direction.

Moreover, the sequence may be represented by a-b-X-c-d or a-c-X-b-d, preferably by a-b-X-c-d, wherein X represents a replication origin. The replication origin includes Ori beta located at the 3' down stream of dihydrofolate reductase (DHFR) gene, latent origin (OriP) of EBV, origins located at the vicinity of c-myc gene or others, as a candidate, and may include any origin with replication initiation activity in animal cells.

Furthermore, the sequence may be represented by a-A-b-X-c-B-d or a-A-c-X-b-B-d, preferably by a-A-b-X-c-B-d, wherein at least one of A and B represents target gene. If a number of target genes are used, they can be the same as or different from each other. DRCR (FIG. 2) explained above are similarly induced in these sequences.

A site-specific recombinase catalyzes the recombination between two short consensus DNA sequences (target sequences). The site-specific recombinase can induce site-specific recombination between the target sequences, change the target site further and modify the integrated gene.

The present invention may use the following site-specific recombinase and the target sequences specific to the recombinase (i.e. see; Developmental Cell, Vol. 6, 7-28, January 2004 and the like).

(1) Cre Recombinase or Derivatives Thereof.

Cre recombinase of bacterial virus P1 is applied most extensively to gene transfer and knockout in mouse. Cre protein catalyzes the recombination between two 34 base pair loxP recognition sites. The loxP sequence has a unique construction, wherein core 8 base pair sequence is flanked by two 13 base pair palindrome sequences. The asymmetric 8 base pair sequence determine the orientation of loxP site. DNA cleavage and recombination between loxP sites by Cre enzyme occur at a site between the rear of the first base and the front of the last base of the 8 base pair core sequence. Derivatives of the Cre enzyme are constructed by amino acid substitutions. The derivatives include site-specific recombinases, wherein wild type Cre recombinase is changed in its function and character by introduction of amino acid substitution; and site-specific recombinases and their genes, wherein mutations are introduced into wild type Cre recombinase gene to optimize CpG content, Kozak sequence related to translation initiation efficiency and codon-usage in host cells to increase expression efficiency and level. At least 29 kinds of Cre enzyme derivatives have been constructed. Derivatives thereof have different recombination activities and recognize different target sequences. Also, a number of mutated sequences are prepared for target sequence recognized by Cre enzyme. The present invention may use all above derivatives. Target sequences like above include loxP, lox511, lox5171, lox2272, lox2372, loxm2 (referred also as m2), loxFAS, lox71, lox 66 and mutants thereof. The mutant refers to a target sequence of site-specific recombination, wherein the sequence contains mutation introduced in one or more bases in wild type loxP sequence.

Although the recombination efficiency is generally sensitive to any change in lox sequences, mutants keeping function thereof were found. In the latter case, recombination may occur efficiently between pairs of homotypic loxP sites, but not between heterotypic sites.

(2) Flp Recombinase or Derivatives Thereof.

The recombinase is Flp recombinase derived from budding yeast. The activity of the recombinase is similar or slightly inferior to that of Cre/loxP. However, the activity of the recently developed active type Flp (Flpe) is improved and is similar to that of Cre. The consensus 34 base recombination sequence is referred to as FRT. Although the structure of FRT has the same structure as loxP, the sequence is different from each other.

Derivatives thereof refer to site-specific recombinases, wherein wild type Flp recombinase is changed in its function and character by introduction of amino acid substitution; and site-specific recombinases and their genes, wherein mutations are introduced into wild type Flp recombinase gene to optimize CpG content, Kozak sequence related to translation initiation efficiency and codon-usage in host cells to increase expression efficiency and level. At least 28 kinds of Flp enzyme derivatives have been constructed.

A number of derivatives have been constructed also for Flp enzyme and its recognition sequence. The target sequence includes FRT, F3, F5, FRT mutant–10, FRT mutant+10 and mutants thereof. The mutant refers to a target sequence of site-specific recombination reaction, wherein the sequence contains mutation introduced in one or more bases of wild type FRT sequence and the like.

Flp enzyme is very sensitive to the change in the sequence of FRT site, similar to Cre enzyme. Several mutant FRT pairs that lead to efficient recombination between homotypic sites are identified. However, recombination does not occur between different mutant FRT sites or between wild and mutant sites.

(3) PhiC31 Integrase or Derivatives Thereof.

PhiC31 integrase is derived from bacterial virus in Streptomyses and is functionable in human cells. The target sequence of the integrase includes attP, attB and their mutants. A mutant refers to a target sequence of the site-specific recombination, wherein the sequence contains mutation in one or more bases in wild type attP sequence and the like.

The enzyme induces recombination between a pair of three nucleotides, ttg, in the attPP' and attBB'. Since the sequences at both sides of 'ttg' are unique, the sequences are changed to different sequences from the original recognition sequences after recombination. Therefore, the enzyme cannot recognize the consequent sequence as a target site. Therefore, the recombination by the enzyme occurs only once.

The derivatives of PhiC31 integrase system refer to site-specific recombinases, wherein wild type PhiC31 integrase is changed in its function and character by introduction of amino acid substitution, and site-specific recombinases and their genes, wherein mutations are introduced into wild type PhiC31 integrase gene to optimize CpG content, Kozak sequence related to translation initiation yield and codon-usage in host cells to increase expression efficiency and level.

Cre/Lox system is preferable among the site-specific recombinase and target sequence thereof.

Furthermore, it is preferable that a target gene to be expressed, selective gene (drug resistant genes for Geneticin, Neomycin, Hygromycin, Zeocin, Blasticidin or the like) for selecting cells that contain the present construct in a chromosome or an extrachromosomal element, and a marker gene (dihydrofolate reductase (DHFR), glutamine synthetase (GS), aspartate transcarbamylase (CAD), metallothionein (MT), adenosine deaminase (ADA), adenylate deaminase (AMPD1,2), UMP synthetase, P-glycoprotein (P-gp), asparagine synthetase (AS), ornithine decarboxylase (ODC) or the like) for selecting cells with gene amplification may be inserted in arbitrary site within the structure. It is preferable to insert nuclear matrix attachment region (MAR) DNA, which is deemed to be important for amplification in animal cells. Additionally, arbitrary DNA sequence could be inserted between the above fragments.

The above fragments are appropriately connected by conventional method of genetic engineering.

The double-stranded DNA fragments thus obtained are transduced into appropriate cells by the methods of virus, lipofection, electroporation or the like. Furthermore, it is preferable to establish cell lines by selecting the cells that contain the above construct on a chromosome or an extrachromosomal element, by the drug corresponding a drug resistant gene (a drug resistant gene to Geneticin, Neomycin, Hygromycin, Zeocin, Blasticidin or the like). Yeast cells and animal cells can be used as the host. Pharmaceutical proteins are produced preferably in animal cells, wherein glycosylation pattern is similar to human and it reduces risk to undesirable immunological response. Animal cells include CHO (Chinese hamster ovary) cells used frequently for protein production as well as other cells derived from human, mouse, rat and other animals.

Furthermore, the double-stranded DNA of the present invention comprises one set of double-stranded DNA fragments obtained by dividing any of the above double-stranded DNA fragments into at least two, preferably 2 to 5, and more preferably two, wherein the DNA fragment comprises partial sequence of a host chromosome or an extrachromosomal element, and may contain at least 50 bp and preferably from 500 to 1 Kbp sequences at both ends for homologous recombination. The double-stranded DNA fragment for homologous recombination can produce the above double-stranded DNA on a host chromosome or an extrachromosomal element by homologous recombination.

The replication origin may be replication origin of the host chromosome or an extrachromosomal element; or an exogenous replication origin.

Moreover, the extrachromosomal element refers to replicable sequence in host cells derived from plasmid or virus, fragments of a host chromosome or an artificial chromosome.

A set of double-stranded DNA fragments thus described include the following examples:

(1) Double-stranded DNA referred to as e-a-A-b-f and double-stranded DNA referred to as g-c-B-d-h;
(2) Double-stranded DNA referred to as e-a-A-f and double-stranded DNA referred to as g-b-c-B-d-h;
(3) Double-stranded DNA referred to as e-a-f and double-stranded DNA referred to as g-A-b-c-B-d-h;
(4) Double-stranded DNA referred to as e-a-A-b-c-f and double-stranded DNA referred to as g-B-d-h;
(5) Double-stranded DNA referred to as e-a-A-b-c-B-f and double-stranded DNA referred to as g-d-h;
(6) Double-stranded DNA referred to as e-a-A-b-B-f and double-stranded DNA referred to as g-d-h;
(7) Double-stranded DNA referred to as e-a-A-f and double-stranded DNA referred to as g-B-d-h;
(8) Double-stranded DNA referred to as e-a-f and double-stranded DNA referred to as g-A-b-B-d-h.

In the above sets of double-stranded DNA, letters from a to d, A and B are similar to the above description. However, d in (6) to (8) refers to the same target sequence with the same orientation as "a".

Letters from e to h refer to the double-stranded DNA fragments comprising nucleotide sequences with size at least 50 bp, and preferably from 500 to 1 Kbp, wherein these DNA fragments are aligned in the order of e, f, replication origin, g, and h on a cellular chromosome or on an extrachromosomal element; and arbitrary sequence may be inserted between these fragments; and replication origin or a part of it may be included in f or g.

These fragments are connected as above.

At least two double-stranded DNA fragments thus obtained are introduced into appropriate cells by methods such as virus, lipofection, electroporation and the like. Furthermore, it is preferable to establish cell lines by selecting the cells that contain the above construct on a chromosome or an extrachromosomal element, by the drug corresponding a drug resistant gene (a drug resistant gene corresponding to Geneticin, Neomycin, Hygromycin, Zeocin, Blasticidin or the like). Yeast cells and animal cells can be used as the host. Pharmaceutical proteins are produced preferably in animal cells, wherein glycosylation pattern is similar to human and it reduces risk to undesirable immunological response.

Owing to the arrangement from e to h in the order and homologous recombination of these fragments with corresponding region in a host chromosome or an extrachromosomal element, similar construction to the above is generated on a host chromosome or on an extrachromosomal element.

The transformed or transfected cells thus obtained are subjected to the action of a site-specific recombinase. At the time of the action, it is preferable that site-specific recombinase works in the cells that are actively proliferating and progressing the cell cycle, or are synchronized in S phase, since enrichment of cells in replication phase (S phase) in cell cycle is preferable.

Methods for introducing the above site-specific recombinase include, for example, a method comprising the following steps:

(1) introducing a plasmid constructed to express said site-specific recombinase;

Various expression vectors are inserted with the site-specific recombinase gene under the control of promoter functional in a host cell. The vector is transfected into the above transformed or transfected cells by lipofection, electroporation method or the like. It is preferable to use inducible promoters to induce site-specific recombinase to actively proliferating cells.

(2) transforming the transformants or transfectants further to express said site-specific recombinase;

A construct, containing the site-specific recombinase gene under the control of promoter functional in a host cell and any of drug resistant genes against Geneticin, Neomycin, Hygromycin, Zeocin, Blasticidin or the like for selecting cells that contain the above construct on a chromosome or an extrachromosomal element, is prepared. The construct is introduced into the above transformed cells by lipofection, electroporation or the like. The construct containing the above DNA fragments is preferably linearized for efficient integration into a chromosome or to an extrachromosomal element. Additionally, inducible promoters are preferably used to induce site-specific recombinase to actively proliferating cells.

(3) introducing directly said site-specific recombinase protein.

Site-specific recombinase is prepared by expressing and purifying large amount of the enzyme. The enzyme is introduced into the above transformed cells using commercial protein delivery reagent (i.e. Targeting System Co., Profect; Genlantis Co., BioPORTER Protein Delivery Reagent) and the like. It is preferable to introduce the site-specific recombinase into cells actively proliferating and progressing the cell cycle, or into cells synchronized in S phase, since the site-specific recombinase should be induced into actively proliferating cells.

In the stage, wherein the site-specific recombinase acts, one of the replication folks must be located between two first target sequences and the other replication folk must be located between two second target sequences after initiation of the replication (FIG. 2 (b)). However, it is not necessary that all of the prepared cells are affected with the site-specific recombinase in such a specific situation. Since practically DNA replication in a number of cells is in various situations, it is enough for part of cells to be in such a specific situation. The target gene is amplified explosively in the cells in the above situation. Therefore, only a fraction of cells are good enough to be amplified.

Although amplification is induced as above description, it is preferable to select the cells with amplified DNA by drugs corresponding to target gene to be amplifieds (dihydrofolate reductase (DHFR), glutamine synthetase (GS), aspartate transcarbamylase (CAD), metallothionein (MT), adenosine deaminase (ADA), adenylate deaminase (AMPD1, 2), UMP synthetase, P-glycoprotein (P-gp), asp aragine synthetase (AS), ornithine decarboxylase (ODC) and the like). Those cell lines with high level of expression of a target gene are thus selected, and cultured. Large amount of the protein encorded by the target gene is prepared by purification from the culture medium or supernatant.

The following examples illustrate the present invention, but are not intended to limit the scope of the present invention.

Example 1

Figure 3:
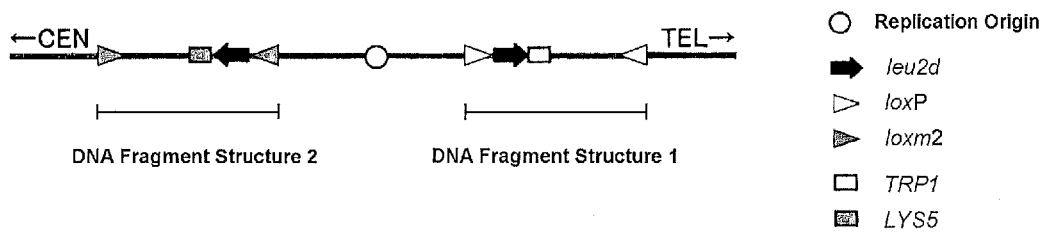
FIG. 3 shows a construct for amplification. CEN: centromere, TEL: telomere.

In this example, a construct (FIG. 3) for amplification was composed.

Firstly, a DNA fragment structure 1 (structure of telomere side) was constructed, wherein the DNA fragment structure 1 contains a pair of loxP sequences with inverted arrangement, amplification-selection marker gene leu2d, and TRP1 gene, (SEQ ID NO.1, bases 1-34 of structure 1 is loxP sequence, bases 36-1988 is amplification marker gene leu2d, bases 1993-2845 (complementary strand) is TRP1 gene, and bases 5699-5732 is loxP sequence of inversion).

A DNA fragment was constructed, wherein the DNA fragment structure 1 is linked PCR fragment of bases 263177-264016 (SEQ ID No. 3) of chromosome 6 (Genebank Accession No. NC_001138) to the upstream of the DNA fragment structure 1 and linked PCR fragment of bases 264017-264685 (SEQ ID No. 4) of chromosome 6 (Genebank Accession No. NC_001138) to the downstream of the DNA fragment structure 1. Host yeast cells lines were transformed with the DNA fragment by Frozen-EZ Yeast Transformation II (ZYMO RESEARCH Co.). TRP1 marker gene allows cells to form colonies on agarose medium without tryptophan. The chromosomal structure of the selected cells was analyzed and cell lines with inserted structure flanked by loxP pair were established.

Then, DNA fragment structure 2 (structure of centromere side) was constructed, wherein the DNA fragment structure 2 contains a pair of loxm2 sequences with inverted arrangement, amplification-selection marker gene leu2d, and LYS5 gene, ((SEQ ID NO.2, bases 1-34 of structure 2 is loxm2 sequence, bases 3936-5888 (complementary strand) is amplification marker gene leu2d, bases 2891-3930 is LYS5 gene, and bases 5890-5923 is loxm2 sequence of inversion)).

A DNA fragment was constructed, wherein the DNA fragment structure 2 is linked PCR fragment of bases 257941-258821 (SEQ ID No. 5) to the upstream of the DNA fragment structure 2 and linked PCR fragment of bases 258822-259719 (SEQ ID No. 6) to the downstream of the DNA fragment structure 2. The DNA fragment was introduced into cells containing the above DNA structure 1 (a structure flanked by loxP pair). LYS5 marker gene allows cells to form colonies on agarose medium without lysine. The chromosomal structure of the selected cells was analyzed and cell lines with inserted structures flanked by loxP pair and loxm2 pair were established.

Additionally, amplification-selection marker gene leu2d lacks most of the promoter sequence and the expression level is very law. Therefore, the gene can complement leucine auxotrophy only when amplified.

It has been observed that Orc1 protein involved in replication initiation binds to the region between the above two DNA fragment structures (nature, 424: 1078, 2003). Therefore, the DNA region is supposed to be functional as replication origin. Furthermore, the DNA region contains WTTTAYRTTTWB (SEQ ID No.: 7), which is a consensus sequence of replication origin in Saccharomyces cerevisiae (bases 258889-258900).

Example 2

In this example, the construct (FIG. 3) obtained in Example 1 was inserted to chromosome 6 of Saccharomyces cerevisiae, Cre gene was expressed and the double rolling-circle replication (DRCR) was induced.

Figure 4:
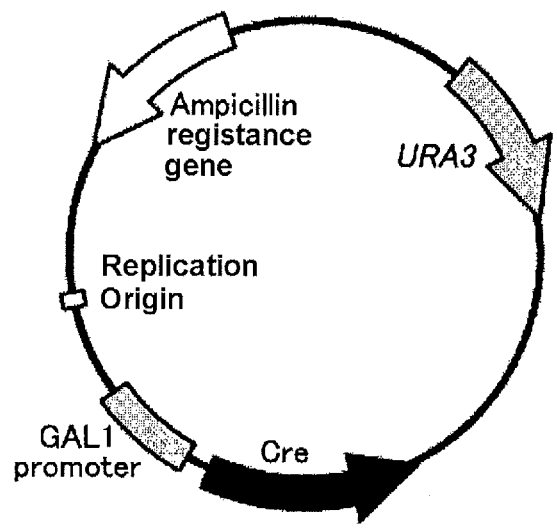
FIG. 4 shows a plasmid (pSH47) for Cre expression.

The plasmid (FIG. 4, Genebank Accession No. AF298782, gifted from University of Washington, Yeast Resource Center), wherein Cre gene (SEQ ID No.:8) is linked to the down stream of GAL promoter, was introduced into Saccharomyces cerevisiae cell line obtained in Example 1 by Frozen-EZ Yeast Transformation II (ZYMO RESEARCH). Furthermore, URA3 marker gene allows cells to form colonies on agarose medium without uracil.

The Ura$^+$ cells with the plasmids obtained above were cultured for three hours in liquid medium supplemented with galactose to induce Cre expression or glucose to suppress Cre expression as control. These cells were plated on glucose agar plate without leucine and then Leu$^+$ colonies were counted. The Leu$^+$ cells were further cultured and chromosomal DNA was prepared using low-melting temperature agarose.

The chromosomal DNA was separated by pulsed-field gel electrophoresis (PFGE, BIO-RAD, CHEF Mapper XA, Auto Algorithm, range: size from 220 to 500 kb), or the DNA digested with a restriction enzyme, SmaI, was separated by Field-inversion gel electrophoresis (FIEG, BIO-RAD, CHEF Mapper XA, Auto Algorism, range: size from 3 to 50 kb) and were analyzed by Southern blotting.

Result and Interpretation

Figure 5:
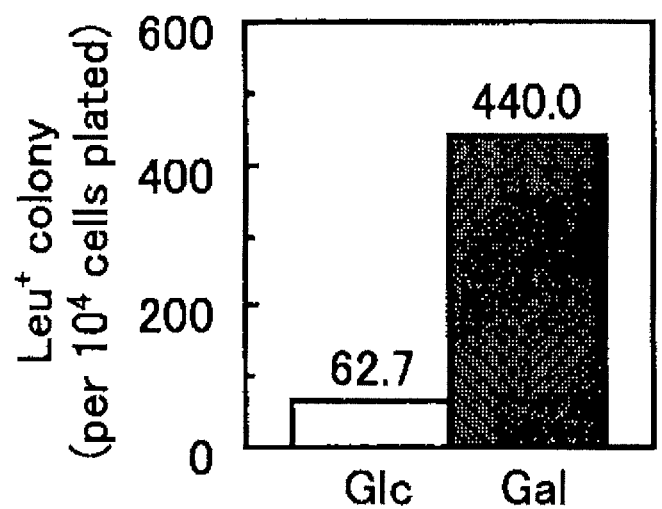
FIG. 5 shows a colony forming frequency. Glc: glucose, Gal: galactose.

The Leu$^+$ colony counts showed that there was about seven folds increase in colony forming activity in the case of induction of Cre expression in contrast to the control (addition of glucose) the induction of Cre expression gave about seven-fold higher frequency of Leu$^+$ colonies than the control condition as shown in FIG. 5. The result strongly suggests that the Cre recombination contributes to the amplification.

Figure 6:
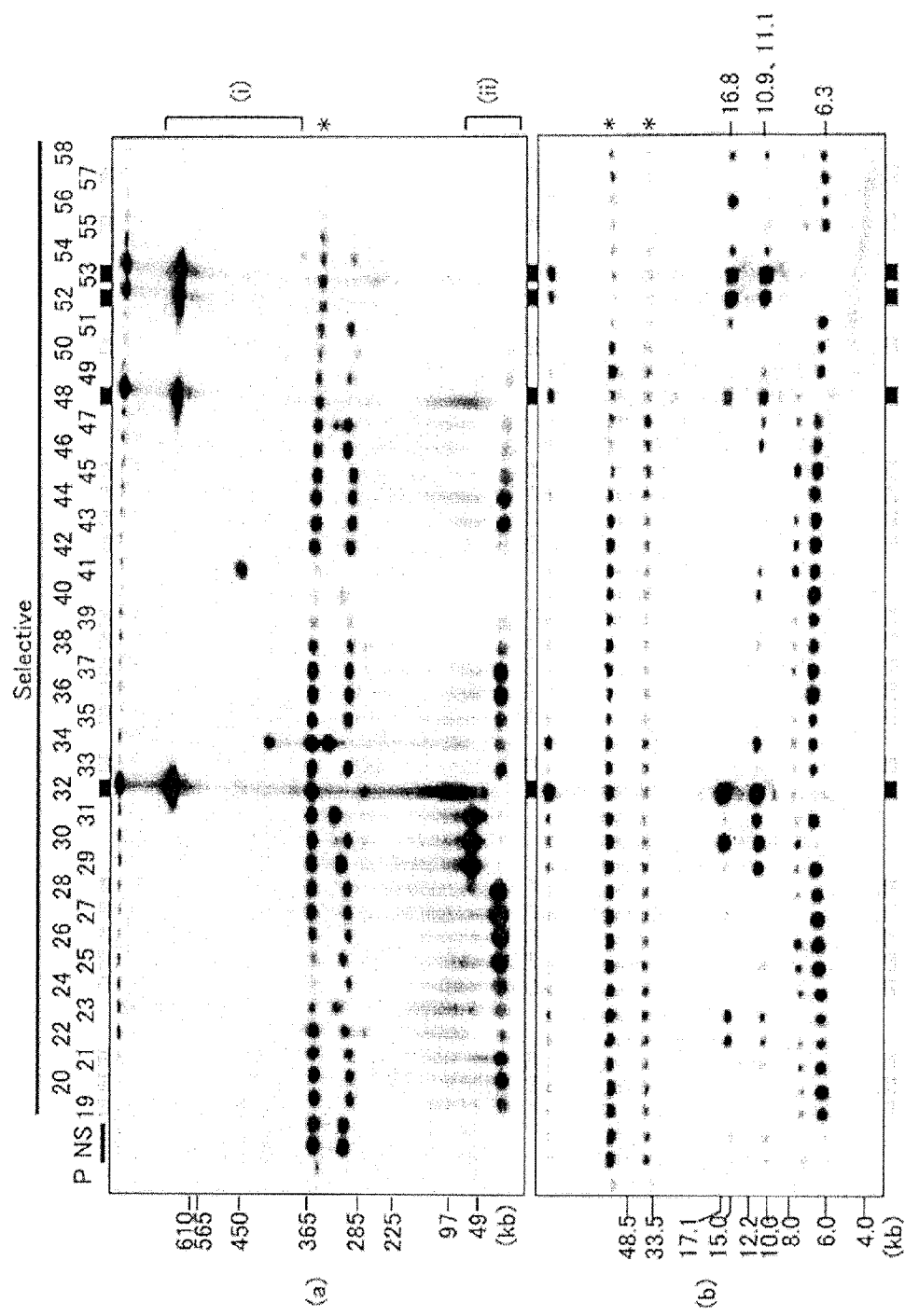
FIG. 6 shows the Southern blot analysis. (a) shows chromosomal DNA separated by PFGE and probed with leu2d, and (b) shows chromosomal DNA digested by SmaI and then separated by FIGE. Lane numbers from #19 to 58 show DNA prepared from colonies grown on the selective medium without leucine after Cre induction by galactose. NS shows DNA from control colonies grown on non-selective medium. P shows host cell lines. In this PFGE conditions, chromosomes with longer than about 650 kb are deemed to be concentrated above the separation limit.

Then, FIG. 6 (a) shows the result of structural analysis of chromosomal DNA, which is separated by PFGE, by Southern blotting using leu2d as a probe. As shown in FIG. 6(a), amplified product (i) on chromosome 6, wherein the construct for amplification is inserted, and (ii) multi-copies of mini-chromosome were detected. Additionally, chromosome 3 (*) of host cell lines containing leu2 fragments at 345 kb in size, chromosome 6 containing the construct for amplification originally (e.g. NS) or containing slight amplification at size from 290 to 320 kb were detected.

Then, the above chromosomal DNA was digested with a restriction enzyme (SmaI) and separated by FIGE. The result of Southern blot for structural analysis using leu2d probe is shown in FIG. 6(b).

Based on these results, the structure of the amplified product was elucidated as follows.

Figure 7:
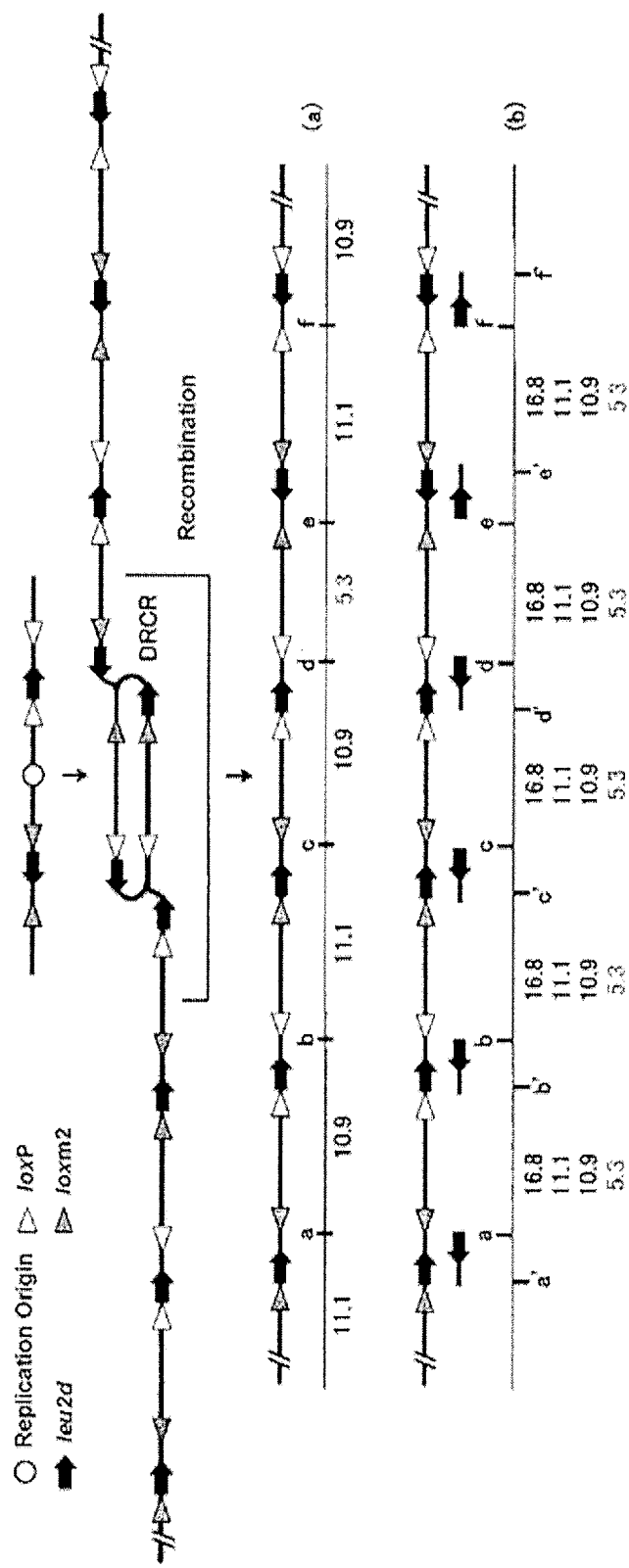
FIG. 7 shows amplified products on chromosome. (a) shows the structure initially generated by DRCR. Letters from a to f represent the cleavage sites by restriction enzyme SmaI and digits show fragment size (kb). Nevertheless, 5.3 kb fragments generated by d-e cleavage are not detected by the Southern blotting, since the fragments do not include leu2d. (b) shows the structure with inversion (rearrangement to reverse direction) of the sequence between lox. Letters from a' to f' represent cleavage sites changed by inversion, and digits show predicted fragment size (kb). For example, a-b cleavage produces 10.9 kb fragment. In a case of inversion of the region containing a, a'-b cleavage produces 16.8 kb fragments. Similarly, a-b' cleavage produces 5.3 kb fragment and a'-b' cleavage produces 11.1 kb fragment. The 5.3 kb fragment, which does not contain leu2d gene, is undetectable by the Southern blotting.

SmaI fragments with about 11 kb (10.9 and 11.1 kb) and 17 kb (16.8 kb) in size were detected from clones with strong signal highly amplified products (i) on chromosome (FIG. 6 (a) (i) #32, 48, 52, 53: black lanes). These fragments were derived from the product with inversions through lox pairs in a designed DRCR product and deemed to contain highly repeated sequence containing leu2d with at least more than several tens of copies, as shown in FIG. 7.

Figure 8:
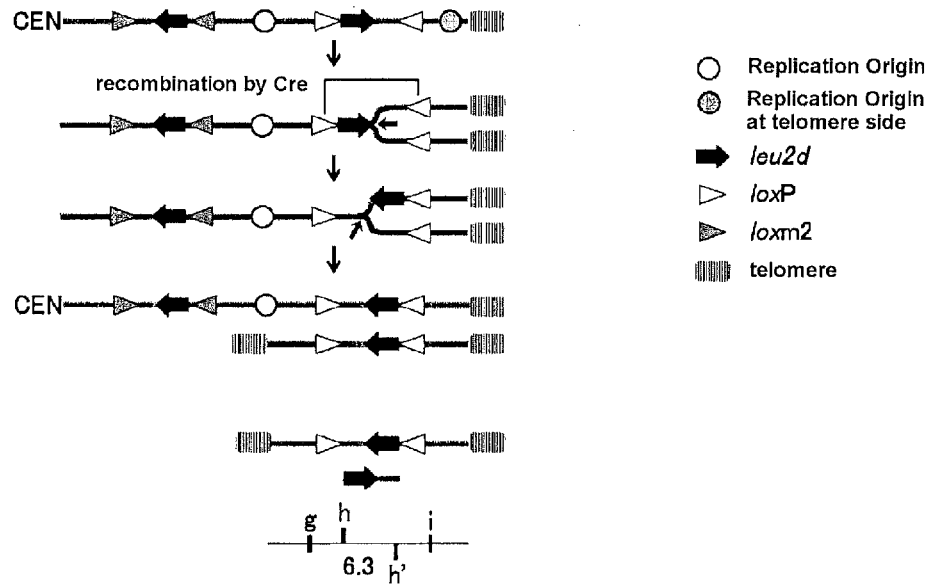
FIG. 8 shows amplified products on a mini chromosome (FIG. 6 (ii)). Replication from the telomere side proceeds to reverse direction due to recombination between loxP, and produces mini chromosome (about 18 kb in size) with telomere at the both ends. The SmaI cleavage sites from g to i and site h' changed by inversion produce 6.3 kb fragments containing leu2d (The fragment is derived from g-h' or h-i fragment. The fragment g-i cannot be generated because of cleavage at either h or h' site).

In contrast, mini chromosome (FIG. 6 (ii)) observed in most of clones (grey lanes) generated SmaI amplified fragments at about 6.3 kb in size. It is interpreted that these fragments are generated through reversal of replication from telomere side of the structure by Cre-loxP recombination, and that these fragments present as multi-copies, as shown in FIG. 8.

Figure 9:
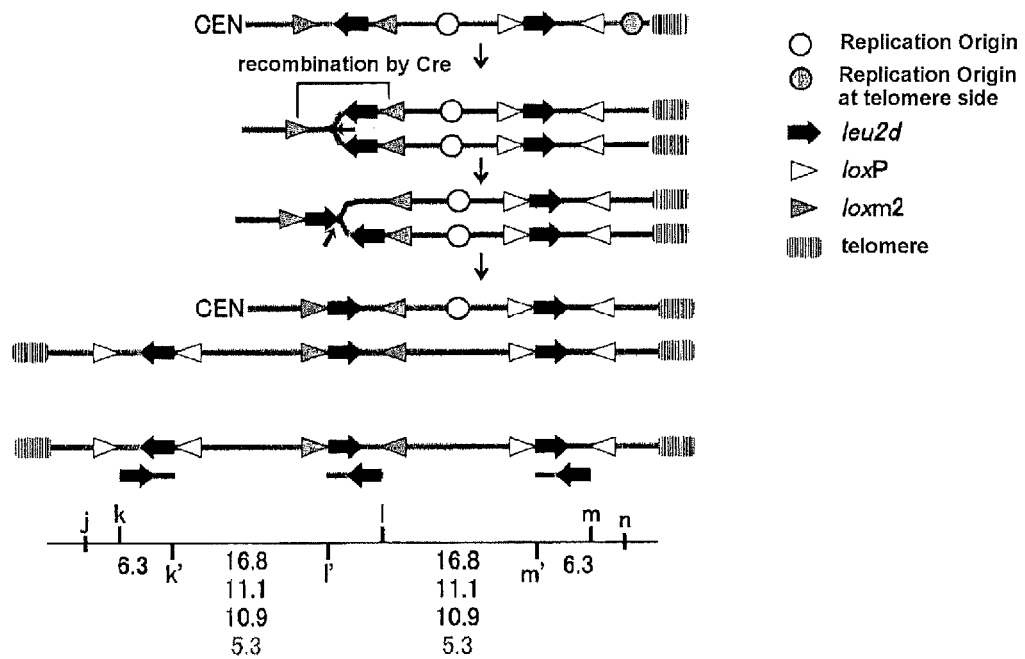
FIG. 9 shows amplification products on a mini chromosome (FIG. 6 (ii)). Replication from the telomere side proceeds to reverse direction due to recombination between loxm2 and produces a mini chromosome (about 40 kb in size). Letters from j to n represent SmaI cleavage sites and letters from k' to m' represent cleavage sites changeable by inversion. Digits show possible fragment size (kb). The 5.3 kb fragment, which does not contain leu2d gene, is undetectable by the Southern blotting.
Figure 10:
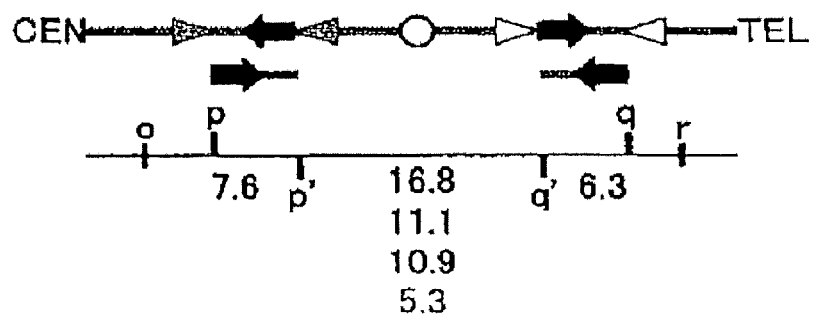
FIG. 10 shows the effect of Cre recombination on not amplified structure. The sequences between lox pairs can be frequently inverted. Letters from o to r represent SmaI cleavage sites, p' and q' represent the cleavage sites changeable by inversion and digits show possible fragment size (kb). The 5.3 kb fragment, which does not contain leu2d gene, is undetectable by the Southern blotting.

In addition to the above fragments, chromosomal products without inversions (FIG. 7(a), #34, 41, 47) and other types of mini chromosome (FIG. 9, #29-31, 49, 56) through reversal of replication by similar recombination are observed. Furthermore, a number of clones containing both amplified product on chromosome and mini chromosome are detected (#22, 31, 34, 41, 47, 58). Also, weak signal originating from four fragments in addition to two SmaI fragments (* of FIG. 6 (b)) derived from host cell lines are confirmed in the construct not amplified (NS of FIG. 6 (b), FIG. 10).

Highly amplified products through the expected molecular mechanism was observed (#32, 48, 52 and 53). Since these products are observed in one tenth of the analyzed clones, these type of amplification occurred at frequency of one tenth of the total colony forming frequency 4.4%, i.e. 0.44%.

What is claimed is:

1. A method for amplifying a target gene, said method comprising:
contacting a transformant with a site-specific recombinase, wherein said transformant comprises a double-stranded DNA represented by a-b-c-d or a-c-b-d, wherein
one of a and b is a double-stranded DNA fragment comprising a first target sequence of a site-specific recombinase, and the other is a double-stranded DNA fragment comprising an inverted sequence of said first target sequence, wherein a first site specific recombination between a and b is induced by the site-specific recombinase; and
one of c and d is a double-stranded DNA fragment comprising a second target sequence of the site-specific recombinase and the other is a double-stranded DNA fragment comprising an inverted sequence of said second target sequence, wherein a second site specific recombination between c and d is induced by the site-specific recombinase;
and wherein
a replication origin and at least one target gene to be amplified are inserted anywhere between a and d;
arbitrary DNA sequences may be inserted among said fragments; and
the first target sequence and the second target sequence of the site-specific recombinase are different; and
the target gene is amplified by Double Rolling-Circle Replication (DRCR) comprising the first site specific recombination and the second site specific recombination.

2. The method of claim 1, wherein contacting the transformant with the site-specific recombinase includes any of the following steps:
(1) introducing a plasmid constructed to express said site-specific recombinase;
(2) transforming said transformant further to express said site-specific recombinase;
(3) introducing directly said site-specific recombinase protein.

3. The method of claim 1, wherein b and c are combined and said double-stranded DNA is represented by a-b-d, wherein a and d are the same sequence with the same direction and the other letters are the same as defined previously.

4. The method of claim 1, wherein the double-stranded DNA is represented by a-b-X-c-d or a-c-X-b-d, wherein X represents a replication origin and the other letters are the same as defined previously.

5. The method of claim 4, wherein the double-stranded DNA is represented by a-A-b-X-c-B-d or a-A-c-X-b-B-d, wherein at least one of A and B represents the target gene, arbitrary DNA sequences may be inserted among these fragments, and the other letters are the same as defined previously.

6. The method of claim 1, wherein each of said the first and the second target sequences is selected from the group comprising loxP, lox511, lox5171, lox2272, lox2372, loxm2, loxFAS, lox71, lox66 and the mutants thereof in a case where the site-specific recombinase is Cre recombinase or its derivative; each of said the first and the second target sequences is selected from the group comprising FRT, F3, F5, FRT mutant−10, FRT mutant+10 and the mutants thereof in a case where the site-specific recombinase is Flp recombinase or its derivative; and each of said the first and the second target sequences is selected from the group comprising attB, attP and the mutants thereof in a case where the site-specific recombinase is phiC31 integrase or its derivative.

7. The method of claim 1, wherein the host is an animal cell.

8. A method for amplifying a target gene, said method comprising:
(a) providing a double-stranded DNA represented by a-b-c-d or a-c-b-d, wherein
one of a and b is a double-stranded DNA fragment comprising a first target sequence of a site-specific recombinase, and the other is a double-stranded DNA fragment comprising an inverted sequence of said first target sequence, wherein a first site specific recombination between a and b is induced by the site-specific recombinase; and
one of c and d is a double-stranded DNA fragment comprising a second target sequence of the site-specific recombinase and the other is a double-stranded DNA fragment comprising an inverted sequence of said second target sequence, wherein a second site specific recombination between c and d is induced by the site-specific recombinase;
and wherein
a replication origin and at least one target gene to be amplified are inserted anywhere between a and d;
arbitrary DNA sequences may be inserted among said fragments; and
the first target sequence and the second target sequence of the site-specific recombinase are different;
(b) obtaining a set of double-stranded DNA fragments by dividing the double stranded DNA of (a) into at least two, wherein
each said fragment contains a double-stranded DNA region with at least 50 bp at both ends for homologous recombination;
said double-stranded DNA region for homologous recombination comprises a part of the sequences of a host chromosome or an extrachromosomal element so that the double-stranded DNA can be integrated into the host chromosome or the extrachromosomal element by homologous recombination; and
said replication origin may be a replication origin of a host or an exogeneous origin;
(c) preparing a transformant, wherein said transformant is prepared by introducing into a host two kinds of the double-stranded DNA of (b), wherein said replication origin locates on a host chromosome or an extrachromosome; and
(d) affecting said transformant with the site-specific recombinase,
wherein the target gene is amplified by Double Rolling-Circle Replication (DRCR) comprising the first site specific recombination and the second site specific recombination.

9. The method of claim 8, wherein the set of double-stranded DNA fragments comprises a double-stranded DNA fragment represented by e-a-A-b-f and a double-stranded DNA fragment represented by g-c-B-d-h, wherein one of a and b is a double-stranded DNA fragment comprising a first target sequence of a site-specific recombinase, and the other is a double-stranded DNA fragment comprising an inverted sequence of said first target sequence; and one of c and d is a double-stranded DNA fragment comprising a second target sequence of the site-specific recombinase and the other is a double-stranded DNA fragment comprising an inverted sequence of said second target sequence; each of letters from e to h is a double-stranded DNA fragment of at least 50 bp in size, which are arranged on a chromosome or an extra-chromosomal element that is a host for integration of the set of double-stranded DNA in order of e, f, a replication origin of the chromosome element or the extrachromosomal element, g and h; at least one of A and B represents the target gene to be amplified; and said replication origin or a part of it may be included in f or g; and an arbitrary DNA sequence may be inserted among these.

10. The method of claim 8, wherein each of said the first and the second target sequences is selected from the group comprising loxP, lox511, lox5171, lox2272, lox2372, loxm2, loxFAS, lox71, lox66 and the mutants thereof in a case where the site-specific recombinase is Cre recombinase or its derivative; each of said the first and the second target sequences is selected from the group comprising FRT, F3, F5, FRT mutant−10, FRT mutant+10 and the mutants thereof in a case where the site-specific recombinase is Flp recombinase or its derivative; and each of said the first and the second target sequences is selected from the group comprising attB, attP and the mutants thereof in a case where the site-specific recombinase is phiC31 integrase or its derivative.

11. The method of claim 8, wherein the host is an animal cell.

12. The method of claim 8, wherein affecting the transformant with the site-specific recombinase includes any of the following steps:
(1) introducing a plasmid constructed to express said site-specific recombinase;
(2) transforming said transformant further to express said site-specific recombinase; and
(3) introducing directly said site-specific recombinase protein.

13. The method of claim 1, wherein the double-stranded DNA is configured to generate in the host, after contacting the transformant with the site-specific recombinase, an amplification product comprising concatenated repeats of the double-stranded DNA between a and d, wherein regions between a and b, and/or between c and d, in the concatenated repeats may or may not be inverted in the amplification product relative to the orientation of corresponding regions in the double-stranded DNA.

14. The method of claim 1, wherein the at least one target gene is amplified during a single cell cycle.

15. The method of claim 1, wherein the replication origin is the replication origin of a host chromosome, fragments of a host chromosome, or an artificial chromosome.

* * * * *

SEQUENCE LISTING

```
<160> NUMBER OF SEQ ID NOS: 8

<210> SEQ ID NO 1
<211> LENGTH: 5732
<212> TYPE: DNA
<213> ORGANISM: Artificial sequence
<220> FEATURE:
<223> OTHER INFORMATION: Artificially synthesized replication unit

<400> SEQUENCE: 1
ataacttcgt ataatgtatg ctatacgaag ttatggatct agaggttaac taagcgaatt      60
tcttatgatt tatgattttt attattaaat aagttataaa aaaaataagt gtatacaaat     120
tttaaagtga ctcttaggtt ttaaaacgaa aattcttatt cttgagtaac tctttcctgt     180
aggtcaggtt gctttctcag gtatagcatg aggtcgctct tattgaccac atctctaccg     240
gcatgccgag caaatgcctg caaatcgctc cccatttcac ccaattgtag atatgctaac     300
tccagcaatg agttgatgaa tctcggtgtg tattttatgt cctcagagga caacacctgt     360
tgtaatcgtt cttccacacg gatcttatat atatttcaag gatataccat tctaatgtct     420
gcccctaaga agatcgtcgt tttgccaggt gaccacgttg gtcaagaaat cacagccgaa     480
gccattaagg ttcttaaagc tatttctgat gttcgttcca atgtcaagtt cgatttcgaa     540
aatcatttaa ttggtggtgc tgctatcgat gctacaggtg tcccacttcc agatgaggcg     600
ctggaagcct ccaagaaggt tgatgccgtt ttgttaggtg ctgtgggtgg tcctaaatgg     660
ggtaccggta gtgttagacc tgaacaaggt ttactaaaaa tccgtaaaga acttcaattg     720
tacgccaact taagaccatg taactttgca tccgactctc ttttagactt atctccaatc     780
aagccacaat ttgctaaagg tactgacttc gttgttgtca gagaattagt gggaggtatt     840
tactttggta agagaaagga agacgatggt gatggtgtcg cttgggatag tgaacaatac     900
accgttccag aagtgcaaag aatcacaaga atggccgctt tcatggccct acaacatgag     960
ccaccattgc ctatttggtc cttggataaa gctaatgttt tggcctcttc aagattatgg    1020
```

```
agaaaaactg tggaggaaac catcaagaac gaattcccta cattgaaggt tcaacatcaa    1080
ttgattgatt ctgccgccat gatcctagtt aagaacccaa cccacctaaa tggtattata    1140
atcaccagca acatgtttgg tgatatcatc tccgatgaag cctccgttat cccaggttcc    1200
ttgggtttgt tgccatctgc gtccttggcc tctttgccag acaagaacac cgcatttggt    1260
ttgtacgaac catgccacgg ttctgctcca gatttgccaa agaataaggt caaccctatc    1320
gccactatct tgtctgctgc aatgatgttg aaattgtcat gaacttgcc tgaagaaggt     1380 aaggccattg aagatgcagt taaaaaggtt ttggatgcag gtatcagaac tggtgattta    1440
ggtggttcca acagtaccac ggaagtcggt gatgctgtcg ccgaagaagt taagaaaatc    1500
cttgcttaaa aagattctct ttttttatga tatttgtaca taaactttat aaatgaaatt    1560
cataatagaa acgacacgaa attacaaaat ggaatatgtt cataggtag acgaaactat      1620 atacgcaatc tacatacatt tatcaagaag gagaaaagg aggatgtaaa ggaatacagg      1680
taagcaaatt gatactaatg gctcaacgtg ataaggaaaa agaattgcac tttaacatta    1740
atattgacaa ggaggagggc accacacaaa aagttaggtg taacagaaaa tcatgaaact    1800
atgattccta atttatatat tggaggattt tctctaaaaa aaaaaaaata caacaaataa    1860 aaacactca atgacctgac catttgatgg agtttaagtc aataccttct tgaaccattt      1920
cccataatgg tgaaagttcc ctcaagaatt ttactctgtc agaaacggcc ttaacgacgt    1980
agtcgacgga tcgatctttt atgcttgctt ttcaaaaggc ctgcaggcaa gtgcacaaac    2040
aatacttaaa taaatactac tcagtaataa cctatttctt agcattttg acgaaatttg       2100 ctattttgtt agagtctttt acaccatttg tctccacacc tccgcttaca tcaacaccaa    2160
taacgccatt taatctaagc gcatcaccaa cattttctgg cgtcagtcca ccagctaaca    2220
taaaatgtaa gctttcgggg ctctcttgcc ttccaaccca gtcagaaatc gagttccaat    2280
ccaaaagttc acctgtccca cctgcttctg aatcaaacaa gggaataaac gaatgaggtt    2340
tctgtgaagc tgcactgagt agtatgttgc agtcttttgg aaatacgagt cttttaataa    2400
ctggcaaacc gaggaactct tggtattctt gccacgactc atctccatgc agttggacga    2460
tatcaatgcc gtaatcattg accagagcca aaacatcctc cttaggttga ttacgaaaca    2520
cgccaaccaa gtatttcgga gtgcctgaac tatttttata tgcttttaca agacttgaaa    2580
ttttccttgc aataaccggg tcaattgttc tctttctatt gggcacacat ataatccca     2640 gcaagtcagc atcggaatct agagcacatt ctgcggcctc tgtgctctgc aagccgcaaa    2700 cttcaccaa tggaccagaa ctacctgtga aattaataac agacatactc caagctgcct      2760
ttgtgtgctt aatcacgtat actcacgtgc tcaatagtca ccaatgccct ccctcttggc    2820
cctctccttt tcttttttcg accgatccgt cgaccgatgc ccttgagagc cttcaaccca    2880
gtcagctcct tccggtgggc gcgggcatg actatcgtcg ccgcacttat gactgtcttc      2940
tttatcatgc aactcgtagg acaggtgccg gcagcgctct tccgcttcct cgctcactga    3000
ctcgctgcgc tcggtcgttc ggctgcggcg agcggtatca gctcactcaa aggcggtaat    3060
acggttatcc acagaatcag gggataacgc aggaaagaac atgtgagcaa aaggccagca    3120
aaaggccagg aaccgtaaaa aggccgcgtt gctggcgttt ttccataggc tccgcccccc    3180
tgacgagcat cacaaaaatc gacgctcaag tcagaggtgg cgaaacccga caggactata    3240
aagataccag gcgtttcccc ctggaagctc cctcgtgcgc tctcctgttc cgaccctgcc    3300
gcttaccgga tacctgtccg cctttctccc ttcgggaagc gtggcgcttt ctcatagctc    3360
acgctgtagg tatctcagtt cggtgtaggt cgttcgctcc aagctgggct gtgtgcacga    3420
```

```
acccccccgtt cagcccgacc gctgcgcctt atccggtaac tatcgtcttg agtccaaccc    3480
ggtaagacac gacttatcgc cactggcagc agccactggt aacaggatta gcagagcgag    3540
gtatgtaggc ggtgctacag agttcttgaa gtggtggcct aactacggct acactagaag    3600
aacagtattt ggtatctgcg ctctgctgaa gccagttacc ttcggaaaaa gagttggtag    3660
ctcttgatcc ggcaaacaaa ccaccgctgg tagcggtggt ttttttgttt gcaagcagca    3720
gattacgcgc agaaaaaaag gatctcaaga agatcctttg atcttttcta cggggtctga    3780
cgctcagtgg aacgaaaact cacgttaagg gattttggtc atgagattat caaaaaggat    3840
cttcacctag atccttttaa attaaaaatg aagttttaaa tcaatctaaa gtatatatga    3900
gtaaacttgg tctgacagtt accaatgctt aatcagtgag gcacctatct cagcgatctg    3960
tctatttcgt tcatccatag ttgcctgact ccccgtcgtg tagataacta cgatacggga    4020
gggcttacca tctggcccca gtgctgcaat gataccgcga gacccacgct caccggctcc    4080
agatttatca gcaataaacc agccagccgg aagggccgag cgcagaagtg gtcctgcaac    4140
tttatccgcc tccatccagt ctattaattg ttgccgggaa gctagagtaa gtagttcgcc    4200
agttaatagt ttgcgcaacg ttgttgccat tgctacaggc atcgtggtgt cacgctcgtc    4260
gtttggtatg gcttcattca gctccggttc ccaacgatca aggcgagtta catgatcccc    4320
catgttgtgc aaaaaagcgg ttagctcctt cggtcctccg atcgttgtca gaagtaagtt    4380
ggccgcagtg ttatcactca tggttatggc agcactgcat aattctctta ctgtcatgcc    4440
atccgtaaga tgcttttctg tgactggtga gtactcaacc aagtcattct gagaatagtg    4500
tatgcggcga ccgagttgct cttgcccggc gtcaatacgg gataataccg cgccacatag    4560
cagaacttta aaagtgctca tcattggaaa acgttcttcg gggcgaaaac tctcaaggat    4620
cttaccgctg ttgagatcca gttcgatgta acccactcgt gcacccaact gatcttcagc    4680
atcttttact ttcaccagcg tttctgggtg agcaaaaaca ggaaggcaaa atgccgcaaa    4740
aaagggaata agggcgacac ggaaatgttg aatactcata ctcttccttt ttcaatatta    4800
ttgaagcatt tatcagggtt attgtctcat gagcggatac atatttgaat gtatttagaa    4860
aaataaacaa atagggggttc gcgcacatt tccccgaaaa gtgccacctg acgcgccctg    4920
tagcggcgca ttaagcgcgg cgggtgtggt ggttacgcgc agcgtgaccg ctacacttgc    4980
cagcgcccta gcgcccgctc ctttcgcttt cttcccttcc tttctcgcca cgttcgccgg    5040
ctttccccgt caagctctaa atcgggggct ccctttaggg ttccgattta gtgctttacg    5100
gcacctcgac cccaaaaaac ttgattaggg tgatggttca cgtagtgggc catcgccctg    5160
atagacggtt tttcgccctt tgacgttgga gtccacgttc tttaatagtg gactcttgtt    5220
ccaaactgga acaacactca accctatctc ggtctattct tttgatttat aagggatttt    5280
gccgatttcg gcctattggt taaaaaatga gctgatttaa caaaaattta acgcgaattt    5340
taacaaaata ttaacgctta caatttgcca ttcgccattc aggctgcgca actgttggga    5400
agggcgatcg gtgcgggcct cttcgctatt acgccagccc aagctaccat gataagtaag    5460
taatattaag gtacgggagg tacttggagc ggccgcaata aaatatcttt attttcatta    5520
catctgtgtg ttggttttt gtgtgaatcg atagtactaa catacgctct ccatcaaaac    5580
aaaacgaaac aaaacaaact agcaaaatag gctgtcccca gtgcaagtgc aggtgccaga    5640
acatttctct atcgataggt accgagctct tacgcgtgct agcccgggct cgagatctat    5700
aacttcgtat agcatacatt atacgaagtt at                                  5732
```

<210> SEQ ID NO 2
<211> LENGTH: 5923
<212> TYPE: DNA
<213> ORGANISM: Artificial sequence
<220> FEATURE:
<223> OTHER INFORMATION: Artificially synthesized replication unit

<400> SEQUENCE: 2

| | | | | | |
|---|---|---|---|---|---|
| ataacttcgt | ataagaaacc | atatacgaag | ttatagatct | cgagcccggg ctagcacgcg | 60 |
| taagagctcg | gtacctatcg | atagagaaat | gttctggcac | ctgcacttgc actggggaca | 120 |
| gcctattttg | ctagtttgtt | ttgtttcgtt | ttgttttgat | ggagagcgta tgttagtact | 180 |
| atcgattcac | acaaaaaacc | aacacacaga | tgtaatgaaa | ataaagatat tttattgcgg | 240 |
| ccgctccaag | tacctcccgt | accttaatat | tacttactta | tcatggtagc ttgggctggc | 300 |
| gtaatagcga | agaggcccgc | accgatcgcc | cttcccaaca | gttgcgcagc ctgaatggcg | 360 |
| aatggcaaat | tgtaagcgtt | aatattttgt | taaaattcgc | gttaaatttt tgttaaatca | 420 |
| gctcatttttt | taaccaatag | gccgaaatcg | gcaaaatccc | ttataaatca aagaataga | 480 |
| ccgagatagg | gttgagtgtt | gttccagttt | ggaacaagag | tccactatta agaacgtgg | 540 |
| actccaacgt | caaagggcga | aaaaccgtct | atcagggcga | tggcccacta cgtgaaccat | 600 |
| caccctaatc | aagttttttg | gggtcgaggt | gccgtaaagc | actaaatcgg aaccctaaag | 660 |
| ggagccccg | atttagagct | tgacggggaa | agccggcgaa | cgtggcgaga aggaaggga | 720 |
| agaaagcgaa | aggagcgggc | gctagggcgc | tggcaagtgt | agcggtcacg ctgcgcgtaa | 780 |
| ccaccacacc | cgccgcgctt | aatgcgccgc | tacagggcgc | gtcaggtggc acttttcggg | 840 |
| gaaatgtgcg | cggaaccccct | atttgtttat | ttttctaaat | acattcaaat atgtatccgc | 900 |
| tcatgagaca | ataaccctga | taaatgcttc | aataatattg | aaaaggaag agtatgagta | 960 |
| ttcaacattt | ccgtgtcgcc | cttattccct | tttttgcggc | attttgcctt cctgtttttg | 1020 |
| ctcacccaga | aacgctggtg | aaagtaaaag | atgctgaaga | tcagttgggt gcacgagtgg | 1080 |
| gttacatcga | actggatctc | aacagcggta | agatccttga | gagttttcgc cccgaagaac | 1140 |
| gttttccaat | gatgagcact | tttaaagttc | tgctatgtgg | cgcggtatta tcccgtattg | 1200 |
| acgccgggca | agagcaactc | ggtcgccgca | tacactattc | tcagaatgac ttggttgagt | 1260 |
| actcaccagt | cacagaaaag | catcttacgg | atggcatgac | agtaagagaa ttatgcagtg | 1320 |
| ctgccataac | catgagtgat | aacactgcgg | ccaacttact | tctgacaacg atcggaggac | 1380 |
| cgaaggagct | aaccgctttt | ttgcacaaca | tgggggatca | tgtaactcgc cttgatcgtt | 1440 |
| gggaaccgga | gctgaatgaa | gccataccaa | acgacgagcg | tgacaccacg atgcctgtag | 1500 |
| caatggcaac | aacgttgcgc | aaactattaa | ctggcgaact | acttactcta gcttcccggc | 1560 |
| aacaattaat | agactggatg | gaggcggata | aagttgcagg | accacttctg cgctcggccc | 1620 |
| ttccggctgg | ctggtttatt | gctgataaat | ctggagccgg | tgagcgtggg tctcgcggta | 1680 |
| tcattgcagc | actggggcca | gatggtaagc | cctcccgtat | cgtagttatc tacacgacgg | 1740 |
| ggagtcaggc | aactatggat | gaacgaaata | gacagatcgc | tgagataggt gcctcactga | 1800 |
| ttaagcattg | gtaactgtca | gaccaagttt | actcatatat | actttagatt gatttaaaac | 1860 |
| ttcattttta | atttaaaagg | atctaggtga | agatcctttt | tgataatctc atgaccaaaa | 1920 |
| tcccttaacg | tgagttttcg | ttccactgag | cgtcagaccc | cgtagaaaag atcaaaggat | 1980 |
| cttcttgaga | tcctttttttt | ctgcgcgtaa | tctgctgctt | gcaaacaaaa aaaccaccgc | 2040 |
| taccagcggt | ggtttgtttg | ccggatcaag | agctaccaac | tctttttccg aaggtaactg | 2100 |

```
gcttcagcag agcgcagata ccaaatactg ttcttctagt gtagccgtag ttaggccacc    2160
acttcaagaa ctctgtagca ccgcctacat acctcgctct gctaatcctg ttaccagtgg    2220
ctgctgccag tggcgataag tcgtgtctta ccgggttgga ctcaagacga tagttaccgg    2280
ataaggcgca gcggtcgggc tgaacggggg gttcgtgcac acagcccagc ttggagcgaa    2340
cgacctacac cgaactgaga tacctacagc gtgagctatg agaaagcgcc acgcttcccg    2400
aagggagaaa ggcggacagg tatccggtaa gcggcagggt cggaacagga gagcgcacga    2460
gggagcttcc aggggaaac gcctggtatc tttatagtcc tgtcgggttt cgccacctct    2520
gacttgagcg tcgattttg tgatgctcgt caggggggcg gagcctatgg aaaaacgcca    2580
gcaacgcggc cttttacgg ttcctggcct tttgctggcc ttttgctcac atgttctttc    2640
ctgcgttatc ccctgattct gtggataacc gtattaccgc ctttgagtga gctgataccg    2700
ctcgccgcag ccgaacgacc gagcgcagcg agtcagtgag cgaggaagcg gaagagcgct    2760
gccggcacct gtcctacgag ttgcatgata agaagacag tcataagtgc ggcgacgata    2820
gtcatgcccc gcgcccaccg gaaggagctg actgggttga aggctctcaa gggcatcggt    2880
cgacggatcc tacataaatg tgagcaagcg aaaaaaaaa attggcatta taaaccatca    2940
ttttcgatga ataatcaat caacgtagat aagctgatat tatataattt tggtctgttc    3000
gtgttgattt tatcactgat ggactttggc atacagatag tgacaattc gttattgaac    3060 cattgagaat ggaaaatcaa tggaacttca tccagagtta tgcacataga agctccctca    3120 gccgaaaaa agctgatagc gccaaaatct attagtgaca agtctgtgtt aaggccagtt    3180
ccagtaaatt ttgtatacga ctccttcaag gaccataagt aagtaaatat tgtgcatgga    3240
tcagacgctt tcagtaaacc gttaaattct ctttcactaa aaacttcttt aaatagctcc    3300
aactcttccc tcccgccata attgcacgga gaagcgatat caattccgac atcctggtat    3360
tcatctgtac ttacacattt tacgaggaac atagctacat attgttcacc gatggtcatg    3420
ctaaatggaa gaaaacgatt gttgtctaag aatggcttac cgaagctgcc cttgtcaaat    3480
ttcagctctt gaaaatttaa gcccgttact atagagcagc caaacaactg cagcagctgg    3540
ctgcatagat ttgaacatct atcgtgaaac gatttttttat tgaggattct ggcttgagac    3600
gccaatggca aagttctcat taatgcctcg aacgtaaact catccgcgag tatatcctct    3660
tgaatttcaa caacgaatat acctgcccat ggtcttacac ctgccacctt tgaaacttcg    3720
cttactactt cagtcgtttt aaccatccac ggttttttg ctgagtgatt ctctttctcc    3780
tcattctcat tttagtcata gcggttttaa taagcgcccg aaagataatt gtaaaacata    3840
tattcaatgc ttaaaaatat aagaaattgc ccatcaattt gaaaactcaa gtaaaacaga    3900
gaagttgtaa ggtgaataag gaatgagtga ggatccgtcg actacgtcgt taaggccgtt    3960
tctgacagag taaaattctt gagggaactt tcaccattat gggaaatggt tcaagaaggt    4020
attgacttaa actccatcaa atggtcaggt cattgagtgt tttttatttg ttgtatttt     4080 tttttttag agaaaatcct ccaatatata aattaggaat catagtttca tgattttctg    4140
ttacacctaa cttttgtgt ggtgccctcc tccttgtcaa tattaatgtt aaagtgcaat    4200
tctttttcct tatcacgttg agccattagt atcaatttgc ttacctgtat tcctttacat    4260
cctccttttt ctccttcttg ataaatgtat gtagattgcg tatatagttt cgtctaccct    4320
atgaacatat tccattttgt aatttcgtgt cgtttctatt atgaatttca tttataaagt    4380
ttatgtacaa atatcataaa aaaagagaat cttttttaagc aaggattttc ttaacttctt    4440
```

```
cggcgacagc atcaccgact tccgtggtac tgttggaacc acctaaatca ccagttctga   4500
tacctgcatc caaaaccttt ttaactgcat cttcaatggc cttaccttct tcaggcaagt   4560
tcaatgacaa tttcaacatc attgcagcag acaagatagt ggcgataggg ttgaccttat   4620
tctttggcaa atctggagca gaaccgtggc atggttcgta caaaccaaat gcggtgttct   4680
tgtctggcaa agaggccaag gacgcagatg gcaacaaacc caaggaacct gggataacgg   4740
aggcttcatc ggagatgata tcaccaaaca tgttgctggt gattataata ccatttaggt   4800
gggttgggtt cttaactagg atcatggcgg cagaatcaat caattgatgt tgaaccttca   4860
atgtagggaa ctcgttcttg atggtttcct ccacagtttt tctccataat cttgaagagg   4920
ccaaaacatt agctttatcc aaggaccaaa taggcaatgg tggctcatgt tgtagggcca   4980
tgaaagcggc cattcttgtg attctttgca cttctggaac ggtgtattgt tcactatccc   5040
aagcgacacc atcaccatcg tcttcctttc tcttaccaaa gtaaatacct cccactaatt   5100
ctctgacaac aacgaagtca gtacctttag caaattgtgg cttgattgga gataagtcta   5160
aaagagagtc ggatgcaaag ttacatggtc ttaagttggc gtacaattga agttctttac   5220
ggatttttag taaaccttgt tcaggtctaa cactaccggt accccattta ggaccaccca   5280
cagcacctaa caaaacggca tcaaccttct tggaggcttc cagcgcctca tctggaagtg   5340
ggacacctgt agcatcgata gcagcaccac caattaaatg attttcgaaa tcgaacttga   5400
cattggaacg aacatcagaa atagcttaa gaaccttaat ggcttcggct gtgatttctt   5460
gaccaacgtg gtcacctggc aaaacgacga tcttcttagg ggcagacatt agaatggtat   5520
atccttgaaa tatatataag atccgtgtgg aagaacgatt acaacaggtg ttgtcctctg   5580
aggacataaa atacacaccg agattcatca actcattgct ggagttagca tatctacaat   5640
tgggtgaaat ggggagcgat ttgcaggcat ttgctcggca tgccggtaga gatgtggtca   5700
ataagagcga cctcatgcta tacctgagaa agcaacctga cctacaggaa agagttactc   5760
aagaataaga atttccgttt taaacctaaa gagtcacttt aaaatttgta tacacttatt   5820
ttttttataa cttatttaat aataaaaatc ataaatcata agaaattcgc ttagttaacc   5880
tctagatcca taacttcgta tatggttct tatacgaagt tat                     5923
```

<210> SEQ ID NO 3
<211> LENGTH: 840
<212> TYPE: DNA
<213> ORGANISM: Saccharomyces cerevisiae

<400> SEQUENCE: 3

```
aggtggagcg caggtcatag gtatgccggc tcattgtttt ctattttaaa aagtaaaaaa     60
tatgctgcta aaggaacacg tgagaaatta cattctccct aggtctgcga taacgcggta    120
atattacact gccgccgcct tccatgcctt tggaaagcag acaatgatgc taggcggcgc    180
ccagcagtat aaactttctc tgcttataac cagaacctct atcacaaaat tagaaactgc    240
gatactatgg gtcagatcga cacataggga gcactattag gcgcaaggcg tatacatagg    300
cattgcgtgt tcaaaaattg tcgtatgaga aaagttccaa actttccacc attactcacc    360
aacaacttac accagcccgg atttaagatt tagcttccga gaatattgtg actcagccac    420
tggtctcttg aatgttgcgt gtagcttgat taagattatg gcataaccgt ttttttact     480 tgcaagagt gaacgtcctt ttactccaaa aggctcctga tgaaactgga gagtctcttt     540
gttctgaaat tttaaagtt tagcacacca tattcacgct cgaggtgaac ccaagttttc     600
ctgaaaaatg tgccatgaac ctgaaaaaaa gaattattct cgaaaataaa aaaggcaatc    660
```

```
aagatcggaa agataagcat ttttttttcaa tccgtatcta acattcataa agtgataaaa    720
aaattgataa cgattttatt gtcgcctctt gttttgagta tattttttta acgttctttt    780
tcggcattca aattccgtat aatcaactca attgtaaggc gccgtagcat ccaaataatg    840
```

<210> SEQ ID NO 4
<211> LENGTH: 669
<212> TYPE: DNA
<213> ORGANISM: Saccharomyces cerevisiae

<400> SEQUENCE: 4

```
ttgaaagtgc caatttgctc atcagtgcta aatattcctt gataaaaata tagaagacaa     60
ggacatataa aaagaaagac tgctctagtg ttgggacacc acaatgaaaa aatacttaac    120
gtgtttcgaa actgtaata taaaattcca gcaaaaacca aatattcac tacaatgatt     180 gatcgtaccg agttatcgaa gtttggtatt actacgcaac tgtctgttat tggacgtaat    240
ccagatgaac aaagtggctt tgttaatcca cctttgtata aggggtcaac catcattctt    300
aaaaaactta gtgatttaga acaaaggaaa ggaagatttt acgggacagc aggttctcca    360
actattgaca atttagaaaa tgcctggacg catttaaccg gcggtgctgg acagtgcta    420 tcagcttctg ggcttggttc tatctctttg gcgctattgg ccctttcgaa agctggtgat    480
catatcttga tgactgatag tgtctacgtg ccaacacgta tgctatgtga tggtttattg    540
gccaagttcg gtgttgaaac ggattattat gacccatcaa tagggaagga tatagaaaaa    600
ctagttaagc caaatacaac cgtcattttc ctcgaaagcc cgggttctgg gaccatggaa    660
gtacaggat                                                            669
```

<210> SEQ ID NO 5
<211> LENGTH: 881
<212> TYPE: DNA
<213> ORGANISM: Saccharomyces cerevisiae

<400> SEQUENCE: 5

```
gcaactaaaa cgcccgtgga ttgaggttca gatttgctac tgtcgctttc gaagaagcta     60
gatgaaccac gggtaaagta ttctgcatct aatgtgttca ataaatattg agtgacgtta    120
tcgtaatgtt acagtactaa caccgctaga aaatgctggt gtgaatgtga atgacgatag    180
acggactgat gcacttttcc attgtacgat aacattactt acaagattgg gagaagcatg    240
attgaaaatt tgactggaag aaccacttat attaggagtg gcggtattag tagaaaattg    300
actaaacgca tccgaaaatt aaatagaatt taaagtttcc ttgggtgcac tgttttgggc    360
tgcagtgcta aaatccagaa gtgttggagt caggttactt gtttgcatac agacattact    420
gaagttttca gaaggccttt gaatcgagaa cgagataagg aagtgtcctc taaatgcaat    480
tttagagctc aaagtgagga tagtggcact gaaacttgat ttagttaatg gcctttagat    540
ttgctgctgt ctgaaaagct catcatcgag aagctcacaa aatggagttc tagttgccct    600
ttcactatac aatcgatgta aagatggctt ataagtattt gaattgtaag ttttgtgcta    660
gctgaggaat caaaaaatgt atttagtgct tccttactgg tcaattgtgt attatttcca    720
gatgaaacag aaaatatgta ttttatggat tgactaatca agtcacttgc tgattgtgta    780
atagtggtgg ttaaagaaag tacagtaagt ttgcttgaaa tacaggcagg attcctggaa    840
tactgcctac tactgcttat tgaatagagt gtaatctcgc c                        881
```

<210> SEQ ID NO 6

```
<211> LENGTH: 898
<212> TYPE: DNA
<213> ORGANISM: Saccharomyces cerevisiae

<400> SEQUENCE: 6
aaacccagta atagcatcgt ttaagaaatg gtgcttactt gtaggtaaaa cttctgaagg      60
atactgagta aatgtaaaat tatatgagtt aaggcagaat gactgtaaac ttttgtgacg     120
aatctggaag atgcattcgt cgattggcct tcattaagtg aagattggta acctattgca     180
tccaaaccag aagtaataca accagaatgt ggagatgagg agccaacagg tgtgtatcca     240
gaaggttcag ccacaggttg gtcatcaata ccactggggg agcatgcaat ataatcagat     300
ggttgcgagg aatagctagt agagctaaaa ctgaacacat tagttaagat tagactagcc     360
atgctcaaag aaacaattag agaggcacct acatgttcgt tatccatttt tgaggaaaaa     420
atagaagtga taataataat tttgctcgaa ctactcgtaa agctacttga aaaacggctc     480
gagattacgg aagagtcggt agtaaaccga ctctcagtgt cacgaatgg aagcgccttg      540
aaactactaa tatcaggtat gcattgaggg gcaaggcaac ctgaatatgc aaagagcata     600
gtcttaactt tcgtagtacg taatacttcg gcattaattt ggcctaccgc tttgccacag     660
ttgagtggtc actggagtat tagccatgaa aaaatgatcc cttgtatatc caggcccaaa     720
gtctaaaatg tacttcctgc caatggttgt cacagctaat attccatttt gaattgactt     780
gatttttaga ttattatcat ggaaccaagt tgatgtcttg caatttctga ttttttaacga    840
tgtactggag gttgacgact aggcaaatct gcgaaacatc ctagtacaat ggcatttg      898

<210> SEQ ID NO 7
<211> LENGTH: 12
<212> TYPE: DNA
<213> ORGANISM: Saccharomyces cerevisiae
<220> FEATURE:
<221> NAME/KEY: misc_feature
<222> LOCATION: (1)..(12)
<223> OTHER INFORMATION: w can be a or t
<220> FEATURE:
<221> NAME/KEY: misc_feature
<222> LOCATION: (1)..(12)
<223> OTHER INFORMATION: y can be c or t
<220> FEATURE:
<221> NAME/KEY: misc_feature
<222> LOCATION: (1)..(12)
<223> OTHER INFORMATION: r can be a or g
<220> FEATURE:
<221> NAME/KEY: misc_feature
<222> LOCATION: (1)..(12)
<223> OTHER INFORMATION: b can be c, g, or t

<400> SEQUENCE: 7
wtttayrttt wb                                                          12

<210> SEQ ID NO 8
<211> LENGTH: 1032
<212> TYPE: DNA
<213> ORGANISM: Bacteriophage P1

<400> SEQUENCE: 8
atgtccaatt tactgaccgt acaccaaaat ttgcctgcat taccggtcga tgcaacgagt      60
gatgaggttc gcaagaacct gatggacatg ttcagggatc gccaggcgtt ttctgagcat     120
acctggaaaa tgcttctgtc cgtttgccgg tcgtgggcgg catggtgcaa gttgaataac     180
cggaaatggt ttcccgcaga acctgaagat gttcgcgatt atcttctata tcttcaggcg     240
cgcggtctgg cagtaaaaac tatccagcaa catttgggcc agctaaacat gcttcatcgt     300
```

```
cggtccgggc tgccacgacc aagtgacagc aatgctgttt cactggttat gcggcggatc      360
cgaaaagaaa acgttgatgc cggtgaacgt gcaaaacagg ctctagcgtt cgaacgcact      420
gatttcgacc aggttcgttc actcatggaa aatagcgatc gctgccagga tatacgtaat      480
ctggcatttc tggggattgc ttataacacc ctgttacgta tagccgaaat tgccaggatc      540
agggttaaag atatctcacg tactgacggt gggagaatgt taatccatat tggcagaacg      600
aaaacgctgg ttagcaccgc aggtgtagag aaggcactta gcctgggggt aactaaactg      660
gtcgagcgat ggatttccgt ctctggtgta gctgatgatc cgaataacta cctgttttgc      720
cgggtcagaa aaaatggtgt tgccgcgcca tctgccacca gccagctatc aactcgcgcc      780
ctggaaggga tttttgaagc aactcatcga ttgatttacg gcgctaagga tgactctggt      840
cagagatacc tggcctggtc tggacacagt gcccgtgtcg gagccgcgcg agatatggcc      900
cgcgctggag tttcaatacc ggagatcatg caagctggtg gctggaccaa tgtaaatatt      960
gtcatgaact atatccgtac cctggatagt gaaacagggg caatggtgcg cctgctggaa      1020
gatggcgatt ag                                                          1032
```